(12) United States Patent
Sommer et al.

(10) Patent No.: US 7,704,374 B2
(45) Date of Patent: Apr. 27, 2010

(54) ELECTROCHEMICAL GAS SENSOR

(75) Inventors: Sabrina Sommer, Luebeck (DE); Herbert Kiesele, Luebeck (DE); Frank Mett, Luebeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 600 days.

(21) Appl. No.: 11/612,726

(22) Filed: Dec. 19, 2006

(65) Prior Publication Data

US 2007/0227910 A1    Oct. 4, 2007

(30) Foreign Application Priority Data

Mar. 30, 2006    (DE) .................. 10 2006 014 713

(51) Int. Cl.
*G01N 27/26* (2006.01)
(52) U.S. Cl. .................. 205/783; 204/431; 204/432; 204/430; 205/785.5; 205/786.5; 205/782
(58) Field of Classification Search ............ 204/430, 204/431, 432; 205/783, 785.5, 786.5, 782
See application file for complete search history.

(56) References Cited

U.S. PATENT DOCUMENTS

| | | | |
|---|---|---|---|
| 3,795,589 A | | 3/1974 | Harald Dahms |
| 4,169,779 A | | 10/1979 | Tataria et al. |
| 4,894,138 A | | 1/1990 | Gambert et al. |
| 2002/0005352 A1 | | 1/2002 | Offenbacher |
| 2002/0033334 A1 | * | 3/2002 | Tschuncky et al. .......... 204/415 |
| 2005/0023270 A1 | | 2/2005 | Hiramatsu et al. |
| 2006/0021881 A1 | * | 2/2006 | Soundarrajan et al. ... 205/777.5 |
| 2006/0266647 A1 | * | 11/2006 | Khalafpour et al. .......... 204/431 |
| 2007/0131550 A1 | * | 6/2007 | Mizutani et al. ............. 204/424 |
| 2007/0227909 A1 | * | 10/2007 | Sommer et al. ........... 205/785.5 |
| 2007/0227910 A1 | * | 10/2007 | Sommer et al. ........... 205/786.5 |
| 2008/0035493 A1 | * | 2/2008 | Sommer et al. ........... 205/786.5 |

FOREIGN PATENT DOCUMENTS

| | | |
|---|---|---|
| DE | 199 39 011 C1 | 1/2001 |
| DE | 101 44 862 A1 | 3/2003 |
| DE | 102004062051 | 7/2006 |
| DE | 102004062052 | 7/2006 |
| DE | 102005020719 B | 9/2006 |
| EP | 1 544 607 A1 | 6/2005 |
| EP | 1 706 130 | 10/2006 |
| GB | 2326485 | 12/1998 |
| GB | 2353363 | 2/2001 |
| GB | 2421578 | 6/2006 |
| GB | 2426343 | 11/2006 |
| JP | 2006234561 | 9/2006 |
| WO | WO 03/046563 | 6/2003 |
| WO | WO 2005/034204 | 4/2005 |
| WO | WO 2005/074467 | 8/2005 |

OTHER PUBLICATIONS

Marion Wienecke, Mihaela-C. Bunescu, Marlis Pietrzak, K. Deistung, Petra Fedtke, PTFE membrane electrodes with increased sensitivity for gas sensor applications: Synthetic Metals, 2003, vol. 138, S. 165-171.

* cited by examiner

*Primary Examiner*—Bruce F Bell
(74) *Attorney, Agent, or Firm*—McGlew and Tuttle, P.C.

(57) ABSTRACT

An electrochemical gas sensor is provided with a carbon-based measuring electrode (3) that it can be used for a large number of electrochemical detection reactions and can be manufactured at a low cost. The measuring electrode (3) contains carbon nanotubes.

34 Claims, 3 Drawing Sheets

ELECTROCHEMICAL GAS SENSOR

CROSS REFERENCE TO RELATED APPLICATIONS

This application claims the benefit of priority under 35 U.S.C. § 119 of DE 10 2006 014 713.8 filed Mar. 30, 2006, the entire contents of which are incorporated herein by reference.

FIELD OF THE INVENTION

The present invention pertains to an electrochemical gas sensor.

BACKGROUND OF THE INVENTION

An electrochemical gas sensor with a plurality of electrodes and a measuring electrode made of diamond-like carbon (DLC) is known from DE 199 39 011 C1. The measuring electrode is produced by means of a coating method, in which diamond-like carbon is applied to a gas-permeable membrane by means of a sputtering method. Measuring electrodes made of DLC have very high long-term stability. However, only a small number of gases can be directly reacted on them, and a mediator is therefore necessary, which oxidizes or reduces the analyte to be measured, while it undergoes reduction or oxidation itself and is again re-oxidized or re-reduced on the measuring electrode. The development of suitable mediators is very demanding, because these must react selectively with the analyte to be measured and must be re-oxidized or re-reduced on the DLC measuring electrode.

An electrochemical gas sensor with a measuring electrode made of boron- or nitrogen-doped diamond (BDD) is disclosed in DE 101 44 862 A1. The measuring electrode material is applied as a thin layer to a porous, gas-permeable substrate. Such measuring electrodes have very high long-term stability and have an extremely large potential window, so that even very difficult-to-oxidize substances (analytes and mediators) can be reacted. Besides the high price compared to other electrode materials, their use in electrochemical gas sensors causes considerable problems in terms of design.

An electrochemical measuring device, in which the measuring electrode has carbon nanotubes, is known from EP 1 544 607 A1. The carbon nanotubes are embedded in an insulator such that contact with the electrolyte is possible on the surface only. Such an electrode design is not suitable for a gas sensor because uniform wetting of the side of the electrode surface facing the gas is not guaranteed.

SUMMARY OF THE INVENTION

The basic object of the present invention is to propose a carbon-based electrode material for an electrochemical gas sensor, which material can be used for a large number of electrochemical detection reactions and can be prepared at low cost.

Measuring electrodes prepared from carbon nanotubes (CNT) have long-term stability, can be integrated in existing sensor constructions in a simple manner, are suitable for a large number of mediators and can be purchased at low cost. There are only a small number of cross sensitivities caused by the electrode material. This applies especially to multiwall carbon nanotubes (MW CNT). Such measuring electrodes are wetted by the electrolyte solution over their entire surface, as a result of which a large surface is obtained for the electrochemical reaction. The measuring electrode according to the present invention is preferably also permeable to gases. A measuring electrode made of CNT has better conductivity than a comparable measuring electrode made of DLC.

Carbon nanotubes have a structural relationship to the fullerenes, which can be prepared, e.g., by evaporating carbon according to a laser evaporation method. A single-wall carbon nanotube has, for example, a diameter of one nm and a length of about 1,000 nm. Besides single-wall carbon nanotubes, there also are double-wall carbon nanotubes (DW CNT) and structures with a plurality of walls (MW CNT).

Carbon nanotubes are provided, due to their production, with metal atoms, e.g., Fe, Ni, Co, including the oxides thereof, so that such carbon nanotubes possess catalytic activities on measuring electrodes. It proved to be advantageous to remove these metal particles by acid treatment.

However, it is possible to bind catalysts or mediators (e.g., porphyrins or phthalocyanines) specifically to the carbon nanotubes. However, it is generally preferable to add a soluble mediator to the electrolyte.

The carbon nanotubes are advantageously applied to a porous carrier, a nonwoven or a diffusion membrane. The carbon nanotubes are put together by self-aggregation or with a binder. Polytetrafluoroethylene (PTFE) powder is preferably used as the binder.

It is especially advantageous to prepare the carbon nanotubes from a prefabricated film, a so-called "buckypaper." The measuring electrode can then be punched out directly from the buckypaper. Large numbers can thus be produced at low cost.

The layer thickness of the carbon nanotubes on the measuring electrode depends on the structure of the measuring electrode.

If the carbon nanotubes are in the form of multiwall carbon nanotubes, the layer thickness is between one $\mu m$ and 1,000 $\mu m$ and preferably between 50 $\mu m$ and 150 $\mu m$. The layer thickness is between 0.5 $\mu m$ and 500 $\mu m$ and preferably between 10 $\mu m$ and 50 $\mu m$ in case of single-wall carbon nanotubes.

The layer thickness also depends on the purity of the material. The layer thickness is rather at the lower end of the range in case of especially pure material.

Due to the use of carbon nanotubes, the material of the measuring electrode will have contact with the analyte or the reacted mediator over a large area, so that complete oxidation or reduction will take place. Part of the analyte or of the reacted mediator is thus prevented from diffusing into the electrolyte space.

The auxiliary electrode preferably consists of a precious metal, e.g., gold, platinum or iridium/iridium oxide or carbon nanotubes.

In addition to the auxiliary electrode, a reference electrode or protective electrode may be present as well.

A sensor according to the present invention for detecting diborane is designed as a three-electrode sensor. The measuring electrode is prepared such that single-wall carbon nanotubes are applied with a layer thickness of 30 $\mu m$ to a gas-permeable membrane. An auxiliary electrode consisting of a precious metal, e.g., platinum, iridium or gold and a reference electrode consisting of iridium/iridium oxide or carbon nanotubes are additionally also present in the sensor housing filled with sulfuric acid.

Gas sensors, whose electrolyte contains a mediator based on transition metal salts of polybasic acids and/or transition metal salts of polyhydroxycarboxylic acids, have especially advantageous properties for detecting and determining $H_2S$ and $SO_2$.

The mediator compounds are specifically compounds that contain at least one other group, selected from among hydroxyl and acid groups, besides at least one acid group. In particular, the mediator compound is a carboxylic acid salt having, besides the one carboxylic acid group, at least one hydroxyl group, preferably at least two hydroxyl groups, and/or at least one additional carboxylic acid group. Tetraborates, such as sodium tetraborate or lithium tetraborate, are also suitable compounds.

Transition metal salts, especially Cu salts of such mediators, permit the selective determination of $SO_2$. However, such mediator compounds can also be used to determine the concentrations of other target gases, e.g., $H_2S$.

It was surprisingly found that the $Fe^{3+}$ salts, such as iron hydrogen phthalate or iron phthalate, are especially suitable among the compounds for use for the determination of $H_2S$. Formation of elemental sulfur was not observed. Contrary to commercially available sensors, such sensors also lack cross sensitivity to $SO_2$.

The mediators indicated possess, furthermore, pH-buffering properties, so that the sensors can be exposed to gas for several hours without loss of sensitivity.

The corresponding $Cu^{2+}$ salts are preferably used to detect or determine $SO_2$.

The mediators are preferably not completely soluble in the liquid gas sensor composition. The use of suspensions or solutions of the mediator with solid offers a number of other advantages, such as:

- Constant mediator concentration with variable air humidity;
- Identical equilibrium potentials at the measuring electrode and the reference electrode if the reference electrode also consists of carbon;
- Filter action of the excess solid; and
- The sensor can be operated under anaerobic conditions if the reference electrode also consists of carbon and the mediator determines the potential of that electrode.

Preferably hygroscopic alkali or alkaline earth metal halides, preferably chlorides, are used as conductive electrolytes in aqueous solution. If organic solvents, e.g., ethylene carbonate and/or propylene carbonate, are used, it is also possible to use, e.g., substituted ammonium salts.

The presence of the mediator offers the possibility of providing sensors that are highly selective to the desired analyte gas by selecting suitable mediators.

The measuring cell contains the measuring electrode and the auxiliary electrode as well as preferably also a protective electrode and reference electrode. The sample contains the electrolyte solution and the redox mediator in the dissolved form and optionally also as an excess solid. The measuring cell has openings, which are provided with a membrane permeable to the analyte and otherwise close the measuring cell to the outside. The electrochemical cell contains a measuring electrode, protective electrode, reference electrode and the auxiliary electrode, which may be arranged in a coplanar, plane-parallel or radial arrangement in relation to one another and are flat. The gap between the plane-parallel electrodes may be filled with a separator, which is permeable to the liquid medium and spaces the electrodes apart.

If a mediator is used, the mode of operation of the measuring cell is as follows: When analyte gas is admitted to the membrane, whether the analyte gas is gaseous or dissolved in a medium, the analyte gas diffuses through the membrane into the electrolyte and is oxidized or reduced by the mediator. The mediator reduced or oxidized in the process is re-oxidized or re-reduced at the measuring electrode.

The most important electrode processes that take place in the area of the measuring electrode shall be briefly explained below on the basis of the example of $Cu^{2+}$ ions as a component of the mediator and of the analyte gas $SO_2$. The $SO_2$ diffusing into the measuring cell from the outside is first oxidized by $Cu^{2+}$ into $SO_4^{2-}$:

$$SO_2 + 2\,H_2O + 2\,Cu^{2+} \leftrightarrows SO_4^{2-} + 2\,Cu^+ + 4H^+.$$

The resulting $Cu^+$ ions are re-oxidized at the measuring electrode:

$$2\,Cu^+ \leftrightarrows 2\,Cu^{2+} + 2\,e^-$$

The electrolyte-mediator mixture according to the present invention can be prepared as follows: So much $CuCl_2$ is added to an LiCl solution that a 0.2-1.0-molar and preferably 0.5-molar $CuCl_2$ will be formed. The sensor has high sensitivity to $SO_2$ with this mediator. However, it has a cross sensitivity to $H_2S$ and elemental sulfur is formed, which leads to clogging of the membrane during prolonged exposure to the gas.

The resulting chloro complex can then be mixed, e.g., with potassium hydrogen phthalate, sodium tetraborate or trisodium citrate. The resulting concentration should preferably agree with the above $CuCl_2$ concentration and be especially about 0.5-molar concentration. A bluish-green precipitate is formed upon the addition of potassium hydrogen phthalate or sodium tetraborate. Copper hydrogen phthalate, copper phthalate and copper tetraborate were described in the literature as dimeric and polymeric compounds. These substances have not yet been used as mediators so far. This also applies to the copper citrate compound, which is likewise available.

Due to the addition of potassium hydrogen phthalate, sodium tetraborate or trisodium citrate, it was possible to markedly reduce the cross sensitivity to $H_2S$, surprisingly to completely eliminate the formation of elemental sulfur and to markedly increase the sensitivity to $SO_2$ and to lower the residual currents.

Exemplary embodiments of the present invention are shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
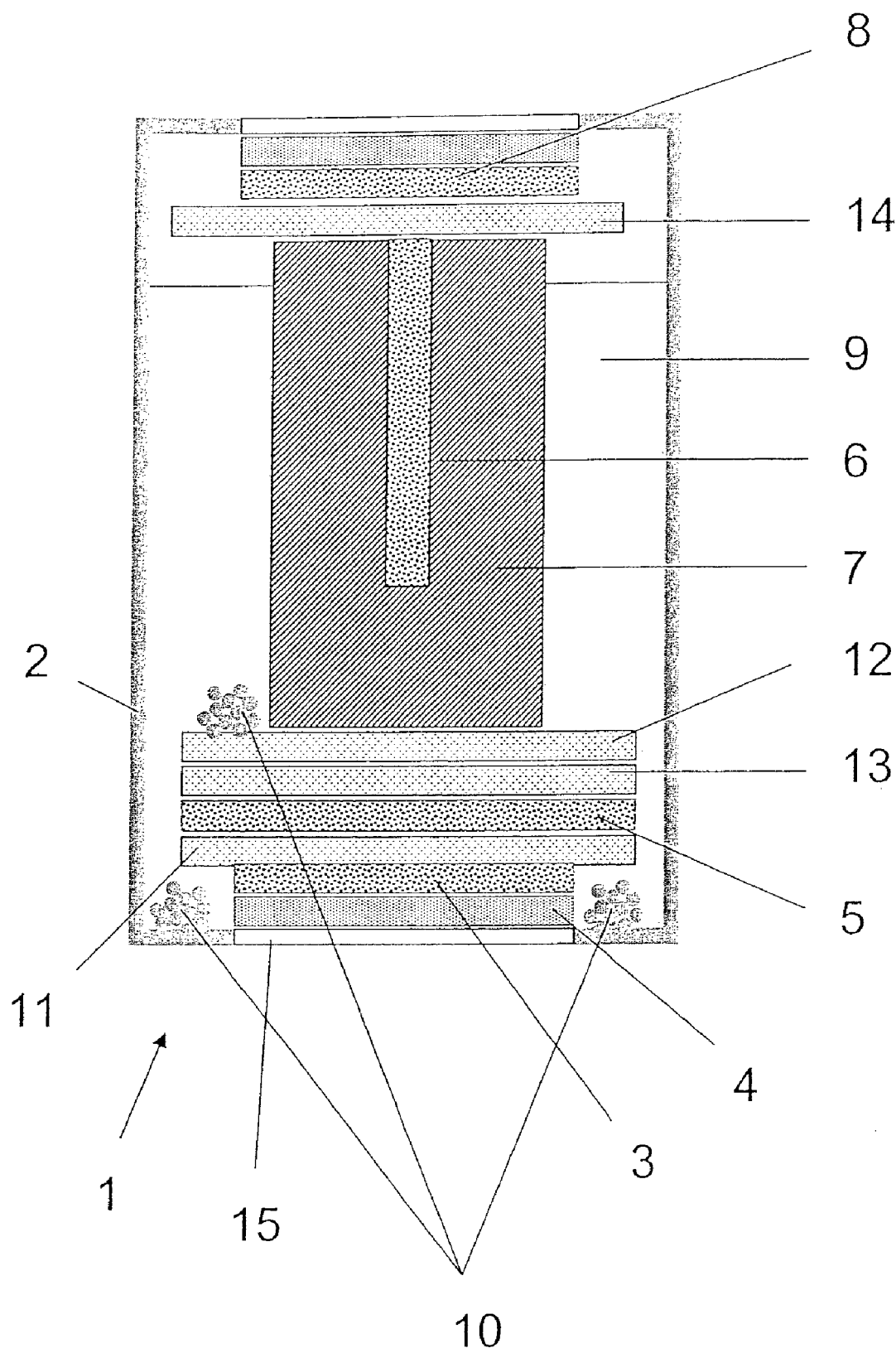
FIG. 1 is a longitudinal sectional view of a first electrochemical gas sensor with an electrolyte-mediator mixture.

Referring to the drawings in particular, a first embodiment of a first electrochemical sensor 1 according to the present invention is shown in FIG. 1. The first electrochemical sensor 1 includes a measuring electrode 3 formed of a layer of carbon nanotubes on a diffusion membrane 4. The measuring electrode 3 and a protective electrode 5, a reference electrode 6 in a wick 7 and an auxiliary electrode 8 are arranged in a sensor housing 2. The interior space of the sensor housing 2 is filled with an electrolyte-mediator mixture 9. The mediator 9 is additionally also present as an excess solid 10. The electrodes 3, 5, 6, 8 are kept at fixed distances from one another by means of liquid-permeable nonwovens 11, 12, 13, 14. The gas enters through an opening 15 in the sensor housing 2. The first electrochemical sensor 1 is connected to a potentiostat, not shown, in the known manner.

Figure 2:
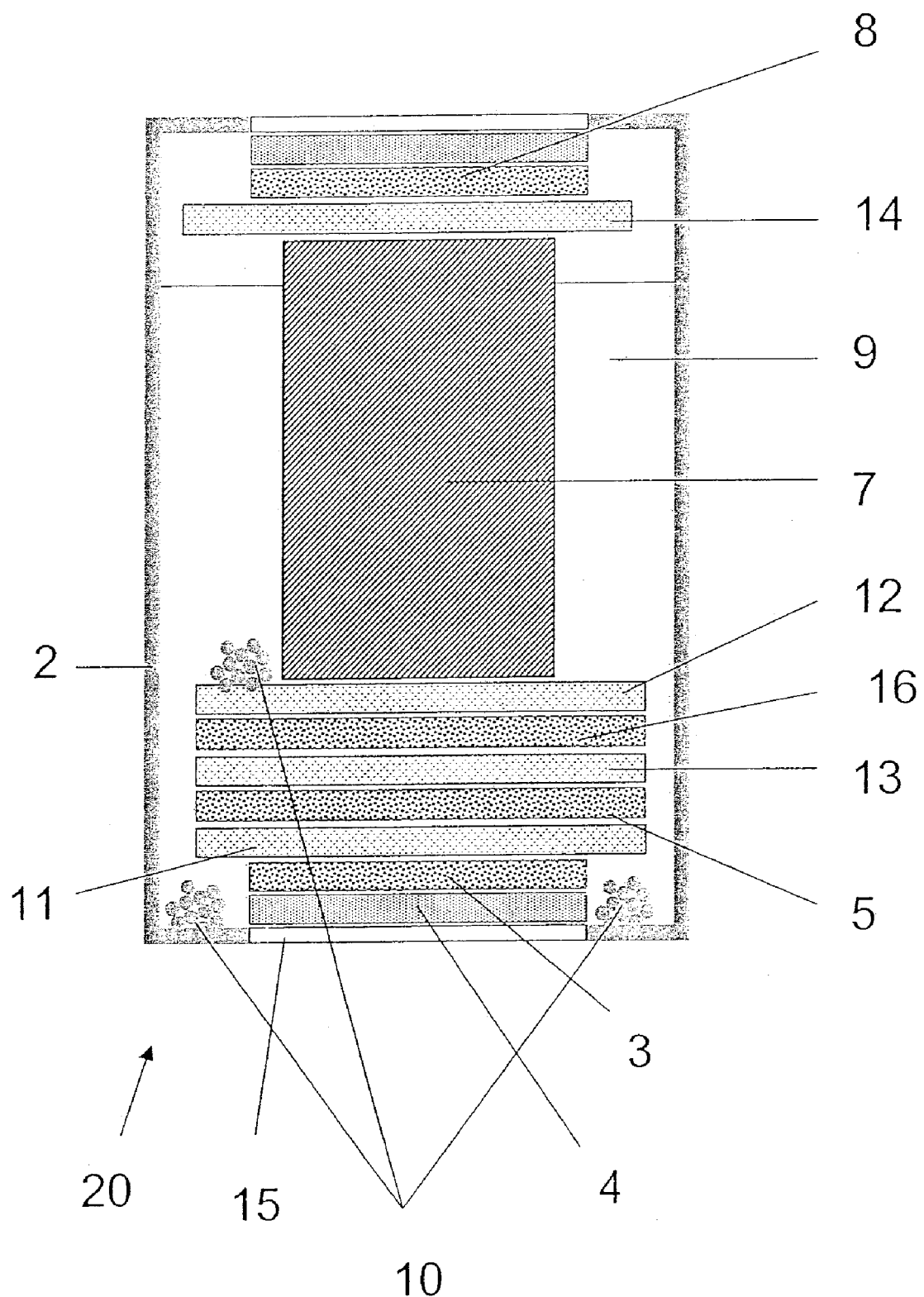
FIG. 2 is a second electrochemical gas sensor according to FIG. 1 with a protective electrode arranged coplanarly with the measuring electrode.

FIG. 2 shows a second electrochemical sensor 20, in which a disk-shaped reference electrode 16 is arranged behind the protective electrode 5, unlike in the first electrochemical sensor 1 according to FIG. 1. Identical components are designated by the same reference numbers as in FIG. 1.

Figure 3:
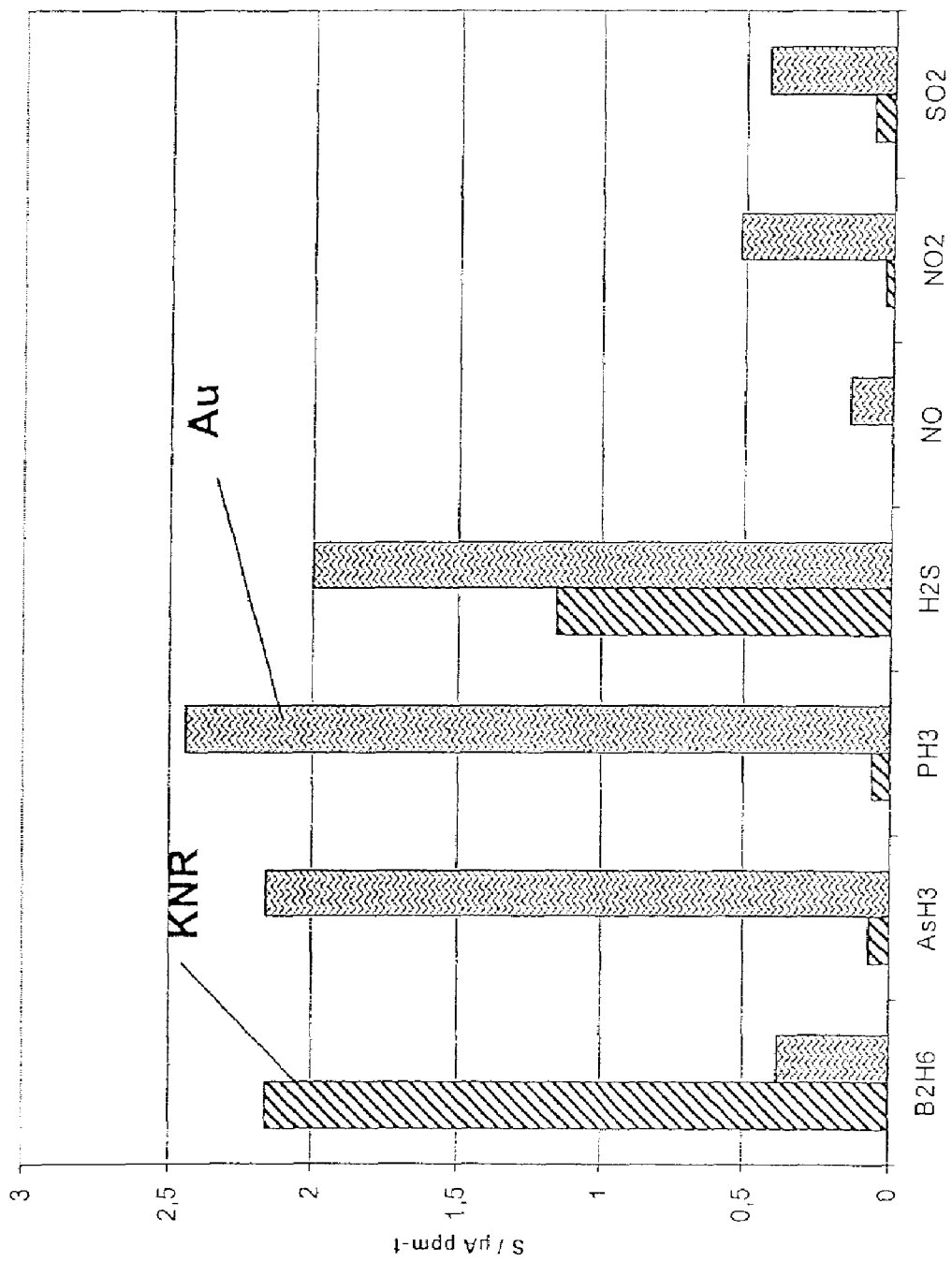
FIG. 3 is the comparison of a conventional electrochemical gas sensor with precious metal electrodes with a gas sensor according to the present invention, which has a measuring electrode with carbon nanotubes.

FIG. 3 illustrates the measured signal characteristic of a conventional three-electrode gas sensor with precious metal electrodes for detecting diborane, $B_2H_6$, with a gas sensor according to the present invention, in which the measuring electrode consists of a 30-µm thick layer of single-wall carbon nanotubes on a gas-permeable membrane. The other electrodes of the gas sensor according to the present invention consists of precious metal, e.g., gold.

The ordinate of FIG. 3 shows the sensitivity and the abscissa the gases in which reactions take place. The heavily shaded bars, CNT, indicate the sensitivity of the gas sensor according to the present invention, while the lightly shaded bars, Au, show the sensitivity of the conventional gas sensor with a measuring electrode made of gold.

It is recognized that the gas sensor according to the present invention has a markedly higher sensitivity in the case of diborane than the conventional sensor and, with the exception of $H_2S$, there are hardly any cross sensitivities to other gases. By contrast, the conventional gas sensor has a comparatively low sensitivity in case of diborane, but has significant cross sensitivities in the case of the gases $AsH_3$, $PH_3$ and $H_2S$. Due to the strong cross sensitivities, it is difficult to select the measured signal for diborane in case of the conventional gas sensor.

While specific embodiments of the invention have been shown and described in detail to illustrate the application of the principles of the invention, it will be understood that the invention may be embodied otherwise without departing from such principles.

What is claimed is:

1. An electrochemical gas sensor for detecting an analyte in a gas sample, the electrochemical gas sensor comprising:
   an electrolyte solution containing a mediator compound, said mediator compound being an acid compound, said acid compound containing either at least two acid groups or at least one hydroxyl group and at least one acid group;
   a measuring electrode in said electrolyte solution, said measuring electrode containing carbon nanotubes; and
   an auxiliary electrode in said electrolyte solution.

2. An electrochemical gas sensor in accordance with claim 1, further comprising a structure comprising one of a porous carrier, a nonwoven material or a diffusion membrane, wherein said carbon nanotubes are located on said structure.

3. An electrochemical gas sensor in accordance with claim 1, wherein said carbon nanotubes are put together by self-aggregation or by means of a binder.

4. An electrochemical gas sensor in accordance with claim 3, wherein said binder is polytetrafluoroethylene (PTFE).

5. An electrochemical gas sensor in accordance with claim 1, wherein said carbon nanotubes are in the form of a film in the form of buckypaper.

6. An electrochemical gas sensor in accordance with claim 1, wherein said carbon nanotubes are in the form of single-wall carbon nanotubes with a layer thickness between 0.5 µm and 500 µm.

7. An electrochemical gas sensor in accordance with claim 1, wherein said carbon nanotubes are in the form of single-wall carbon nanotubes with a layer thickness between 10 µm to 50 µm.

8. An electrochemical gas sensor in accordance with claim 1, wherein said carbon nanotubes are in the form of multiwall carbon nanotubes with a layer thickness between 1 µm and 1,000 µm.

9. An electrochemical gas sensor in accordance with claim 1, wherein said carbon nanotubes are in the form of multiwall carbon nanotubes with a layer thickness between 50 µm and 150 µm.

10. An electrochemical gas sensor in accordance with claim 1, wherein said auxiliary electrode consists of a precious metal.

11. An electrochemical gas sensor in accordance with claim 1, wherein said auxiliary electrode comprises at least one of gold, platinum or iridium or carbon nanotubes.

12. An electrochemical gas sensor in accordance with claim 1, wherein a reference electrode is additionally present.

13. An electrochemical gas sensor in accordance with claim 1, wherein a protective electrode is arranged behind said measuring electrode.

14. An electrochemical gas sensor in accordance with claim 1, wherein molecular structures with catalytic activity or mediator properties are bound to said carbon nanotubes.

15. An electrochemical gas sensor in accordance with claim 14, wherein said molecular structures contain transition metals like one of Fe, Ni, Co, or corresponding metal oxides.

16. An electrochemical gas sensor in accordance with claim 14, wherein said molecular structures contain transition metal complexes including at least one of porphyrins or phthalocyanines.

17. An electrochemical gas sensor in accordance with claim 1, wherein said electrolyte solution is present as an aqueous or organic electrolyte.

18. An electrochemical gas sensor in accordance with claim 17, wherein said organic electrolyte solution is selected from the group of carbonates.

19. An electrochemical gas sensor in accordance with claim 17, wherein said organic electrolyte solution comprises propylene carbonate mixed with ethylene carbonate and/or higher carbonates.

20. An electrochemical gas sensor in accordance with claim 1, wherein the acid compound is a carboxylic acid.

21. An electrochemical gas sensor in accordance with claim 20, wherein said carboxylic acid is an aromatic carboxylic acid containing two or three carboxyl groups.

22. An electrochemical gas sensor in accordance with claim 21, wherein said carboxyl groups comprise phthalic acid, isophthalic acid or terephthalic acid.

23. An electrochemical gas sensor in accordance with claim 1, wherein acid compound is an aliphatic polycarboxylic acid, especially citric acid.

24. An electrochemical gas sensor in accordance with claim 1, wherein the acid compound is gluconic acid.

25. An electrochemical gas sensor in accordance with claim 1, wherein the acid compound is boric acid.

26. An electrochemical gas sensor in accordance with claim 1, wherein said electrolyte solution contains alkali or alkaline earth metal salts.

27. An electrochemical gas sensor in accordance with claim 26, wherein said electrolyte solution contains LiCl.

28. An electrochemical gas sensor in accordance with claim 1, wherein water or organic solvents, ethylene and/or propylene carbonate, are used as a solvent.

29. An electrochemical gas sensor in accordance with claim 1, wherein a transition metal salt is a copper salt or $Cu^{2+}$ salt.

30. An electrochemical gas sensor in accordance with claim 29, wherein the $Cu^{2+}$ salt is $CuCl_2$ and the concentration of $CuCl_2$ is between one of 0.1 mol and 1.0 mol, 0.5 mol in a 0.5-10-molar preferably 5-molar LiCl solution.

31. An electrochemical gas sensor in accordance with at least claim 1, wherein a transition metal salt is an iron salt or $Fe^{3+}$ salt.

32. A method of electrochemical gas sensing, the method comprising:
    providing an electrolyte solution containing a mediator compound, said mediator compound being an acid compound, said acid compound containing either at least two acid groups or at least one hydroxyl group and at least one acid group;
    providing a measuring electrode in said electrolyte solution, said measuring electrode containing carbon nanotubes; and
    providing an auxiliary electrode in said electrolyte solution.

33. A method of electrochemical gas sensing in accordance with claim 32, further comprising:
    determining $SO_2$ concentration in a gas wherein the electrolyte is or contains a chloride.

34. A method of electrochemical gas sensing in accordance with claim 32, further comprising;
    determining $H_2S$ concentration in a gas wherein said electrolyte is or contains a chloride.

* * * * *